United States Patent
Fulara et al.

(10) Patent No.: US 9,670,106 B2
(45) Date of Patent: Jun. 6, 2017

(54) PRESSURISED RECIRCULATION OF ORGANIC MATERIAL

(75) Inventors: Janusz Krzysztof Fulara, Kallaroo (AU); Martin Richard Gravett, Salisbury (AU); Sean Neil Sciberras, Sorrento (AU); Lee Richard Walker, High Wycombe (AU)

(73) Assignee: ANAECO LIMITED, Bentley (AU)

( * ) Notice: Subject to any disclaimer, the term of this patent is extended or adjusted under 35 U.S.C. 154(b) by 286 days.

(21) Appl. No.: 14/240,642

(22) PCT Filed: Sep. 6, 2012

(86) PCT No.: PCT/AU2012/001058
§ 371 (c)(1),
(2), (4) Date: May 15, 2014

(87) PCT Pub. No.: WO2013/033773
PCT Pub. Date: Mar. 14, 2013

(65) Prior Publication Data
US 2014/0311198 A1    Oct. 23, 2014

(30) Foreign Application Priority Data
Sep. 6, 2011  (AU) ................................ 2011903621

(51) Int. Cl.
*C05F 17/00*    (2006.01)
*C05F 17/02*    (2006.01)
(Continued)

(52) U.S. Cl.
CPC ............. *C05F 17/02* (2013.01); *C05F 17/00* (2013.01); *C05F 17/0027* (2013.01);
(Continued)

(58) Field of Classification Search
CPC .. C05F 17/0027; C05F 17/0264; C05F 17/00; C05F 17/02; C12M 21/04; C12M 29/14;
(Continued)

(56) References Cited

U.S. PATENT DOCUMENTS 2,878,112 A     3/1959  Morrison
4,511,370 A  *  4/1985  Hunziker et al. ...... C12M 21/04
                                                    210/603
(Continued)

FOREIGN PATENT DOCUMENTS

CN    1371344 A    9/2002
CN    1656043 A    8/2005
(Continued)

OTHER PUBLICATIONS

Office Action issued in Chinese Patent Application No. 201280053441.7 on May 4, 2015 along with English translation, 16 pages.
(Continued)

*Primary Examiner* — Gautam Prakash
(74) *Attorney, Agent, or Firm* — Rothwell, Figg, Ernst & Manbeck, P.C.

(57) ABSTRACT

An apparatus (10) for the pressurized recirculation of organic material comprising a reactor vessel (12) capable of being pressurized and in which both anaerobic digestion and aerobic composting of organic material may occur, the reactor vessel (12) having both an inlet (14) and an outlet (16) for organic material, together with a conveyor means (18, 20, 22, 28, 29, 30, 32, 34 and 36) to convey organic material to the inlet (14) and from the outlet (16), whereby organic material may be transferred between the outlet (16) and the inlet (14) to achieve recirculation and rearrangement (Continued)

thereof while maintaining a pressurized state. A method for the pressurized recirculation of organic material is also described.

8 Claims, 1 Drawing Sheet

(51) Int. Cl.
*C12M 1/107* (2006.01)
*C12M 1/00* (2006.01)
*C12M 1/26* (2006.01)
*C12M 1/16* (2006.01)

(52) U.S. Cl.
CPC ......... *C05F 17/0264* (2013.01); *C12M 21/04* (2013.01); *C12M 21/16* (2013.01); *C12M 29/14* (2013.01); *C12M 29/18* (2013.01); *C12M 33/16* (2013.01); *C12M 33/20* (2013.01); *Y02P 20/145* (2015.11); *Y02W 30/43* (2015.05); *Y02W 30/47* (2015.05)

(58) Field of Classification Search
CPC ...... C12M 33/20; C12M 21/16; C12M 33/16; C12M 29/18; Y02P 20/145; Y02W 30/47; Y02W 30/43
See application file for complete search history.

(56) References Cited

U.S. PATENT DOCUMENTS

| | | |
|---|---|---|
| 6,299,774 B1 | 10/2001 | Ainsworth et al. |
| 7,160,456 B2 | 1/2007 | Järventie |
| 2004/0164020 A1 | 8/2004 | De Baere et al. |
| 2004/0173526 A1 | 9/2004 | Leskow |
| 2010/0213141 A1* | 8/2010 | Griffin et al. ............ B01D 1/14 210/774 |

FOREIGN PATENT DOCUMENTS

| | | |
|---|---|---|
| CN | 101421194 A | 4/2009 |
| EP | 0172443 A1 | 2/1986 |
| EP | 974643 A1 | 1/2000 |
| GB | 748297 A | 4/1956 |
| KR | 10-0722407 B1 | 5/2007 |
| WO | 2010/118103 A1 | 10/2010 |

OTHER PUBLICATIONS

Supplementary European Search Report issued in European Patent Application No. 12830527.3 on Jul. 10, 2015, 6 pages.
Third Office Action issued in corresponding Chinese patent application No. 201280053441.7 dated Jul. 8, 2016 including English translation, 17 pages.

* cited by examiner

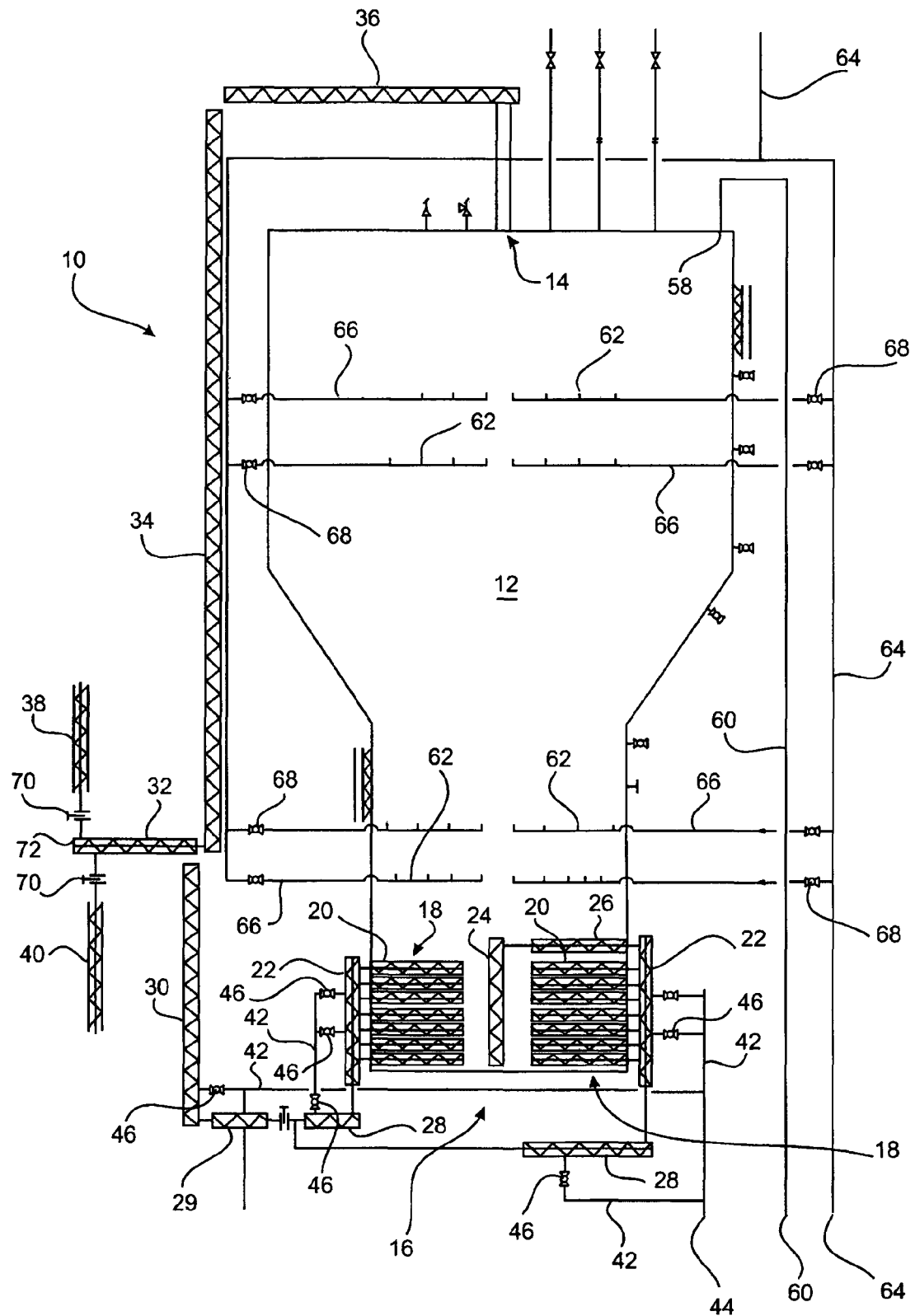

PRESSURISED RECIRCULATION OF ORGANIC MATERIAL

CROSS REFERENCE TO RELATED APPLICATIONS

This application is a 35 U.S.C. §371 National Phase Entry Application from PCT/AU2012/001058, filed Sep. 6, 2012, and designating the United States, which claims priority under 35 U.S.C. §119 to Australian Provisional Patent Application No. 2011903621 filed Sep. 6, 2011, which is incorporated herein in its entirety.

FIELD OF THE INVENTION

The present invention relates to the pressurised recirculation of organic material. More particularly, the present invention is intended to allow the pressurised recirculation of the organic fraction of municipal solid waste ("OFMSW") within a system provided for the digestion of OFMSW and the production of biogas therefrom, thereby increasing the economics of that system.

BACKGROUND ART

It is known that solid organic waste material may be treated under either anaerobic or aerobic conditions to produce a bioactive, stable end product that, for example, may be used as compost for gardens. This process is achieved through the action of, respectively, anaerobic or aerobic microorganisms that are able to metabolise the organic waste material to produce the bioactive, stable end product.

It is also known that the aerobic decomposition of solid organic waste material takes place in the presence of oxygen. The temperature of the waste material rises as the energy produced during aerobic decomposition is released as heat, often reaching temperatures of approximately 75° C. under ambient conditions. The solid end product is often rich in nitrates which are a readily bio-available source of nitrogen for plants, making the end product particularly suitable as a fertiliser.

It is further known that the anaerobic digestion of solid organic waste material takes place in, the absence of oxygen. Anaerobic microbial metabolism is understood to be optimised when the organic material is heated to temperatures at which mesophilic or thermophilic bacteria are operative. The process of anaerobic microbial metabolism results in the production of biogas, in turn predominantly methane and carbon dioxide. The solid product of the process is often rich in ammonium salts. Such ammonium salts are not readily bio-available and are, consequently, generally treated under conditions in which aerobic decomposition will occur. In this manner the material is used to produce a product that is bio-available.

Typically, systems for the biodegradation of organic waste material are directed to either aerobic or anaerobic processes. However, there are a small number of systems that have sought to combine both anaerobic and aerobic biodegradation processes. The processes of German Patent 4440750 and International Patent Application PCT/DE1994/000440 (WO 1994/024071) each describe the combination of an anaerobic fermentation unit and an aerobic composting unit. Importantly, these systems describe discrete and separate vessels for the aerobic and anaerobic biodegradation processes.

International Patent Application PCT/AU00/00865 (WO 01/05729) describes an improved process and apparatus in which many of the inefficiencies of the previous processes and apparatus are overcome. The improved process and apparatus are characterised at a fundamental level by the sequential treatment of organic waste material in a single vessel, through an initial aerobic step to raise the temperature of the organic waste material, an anaerobic digestion step and a subsequent aerobic treatment step. During the anaerobic digestion step a process water or inoculum containing micro organisms is introduced to the vessel to create conditions suitable for efficient anaerobic digestion of the contents and the production of biogas. The introduced inoculum also aids in heat and mass transfer as well as providing buffer capacity to protect against acidification. Subsequently, air is introduced to the residues in the vessel to create conditions for aerobic degradation. It is further described that the water introduced during anaerobic digestion may be sourced from an interconnected vessel that has undergone anaerobic digestion.

Given the relative size of the vessel, the OFMSW is subjected to relatively high and varied consolidation pressures, which results in a diminished, or reduced, capacity for the liquid introduced during the anaerobic digestion to penetrate all parts of the material within the vessel. As such, there is a reduced biogas yield from the OFMSW. Therefore, it is desirable to recirculate the OFMSW during anaerobic digestion in order to improve liquid penetration into the OFMSW. This in turn is expected to lead to greater biogas production.

Additionally, the sequential treatment of the OFMSW in the single vessel through anaerobic digestion and aerobic, composting stages brings with it certain challenges, resulting in part from the fundamentally 'batch' nature of the process. That is, compared to other prior art processes in which the OFMSW is simply transferred to another reactor between stages care is needed to ensure that conditions are transitioned through to those most suitable for each stage when the other stage has finished. This requires that a certain amount of time be taken in these transitions. One such problematic transition is the change from anaerobic digestion to aerobic composting. In order for this change to occur as quickly as possible it is necessary for the dewatering of the solids.

Finally, it is also desirable to maintain a certain moisture content after the anaerobic digestion to aerobic composting transition. It is further desirable to achieve this transition without having to open the reactor vessel to atmosphere. The present invention has as one object thereof to overcome substantially the abovementioned problems of the prior art, or to at least provide a useful alternative thereto.

Korean Patent 10-0722407 to Sib Co., Ltd discloses a high pressure and temperature aerobic digester intended for the treatment of high strength waste water, including livestock excreta. The specification describes an air-lift reactor that utilises downward liquid flow through a central column or "circulation induction pipe". The elevated pressure is said to enhance oxygen transfer and dissolution, and the metabolism of the high temperature aerobic microorganisms present is said to heat the recirculated liquid. This is further said to process the "high concentration organic waste water" within a time frame of 3 to 5 days. Specifically, it is the water or liquid that is recirculated within the aerobic digester vessel. This occurs by way of forced convection or "air lift". The digester described in this Korean patent does not provide a solution to the recirculation of solid materials under pressure.

The preceding discussion of the background art is intended to facilitate an understanding of the present invention only. The discussion is not an acknowledgement or admission that any of the material referred to is or was part of the common general knowledge as at the priority date of the application.

Throughout the specification and claims, unless the context requires otherwise, the word "comprise" or variations such as "comprises" or "comprising", will be understood to imply the inclusion of a stated integer or group of integers but not the exclusion of any other integer or group of integers.

DISCLOSURE OF THE INVENTION

In accordance with the present invention there is provided an apparatus for the pressurised recirculation of organic material comprising a reactor vessel capable of being pressurised and in which both anaerobic digestion and aerobic composting of organic material may occur, the reactor vessel having both an inlet and an outlet for organic material, together with a conveyor means to convey organic material to the inlet and from the outlet, whereby organic material may be transferred between the outlet and the inlet to achieve recirculation and rearrangement thereof whilst maintaining a pressurised state.

Preferably, the conveyor means are located at least in part externally to the reactor and are arranged so as to allow the maintenance of pressurised conditions therein.

Still preferably, the conveyor means is comprised of a series of individual conveyors.

The organic material being conveyed is preferably organic solids. In one form of the present invention the organic solids are the organic fraction of municipal solid waste.

One or more of the individual conveyors are preferably provided with dewatering means. In one form at least a portion of the dewatering means may be provided in the form of 180° screens. In another form at least a portion of the dewatering means may be provided as one or more dewatering presses.

Preferably, the moisture content of the conveyed organic material is reduced to about 40 to 60% prior to the inlet.

The conveyor means are preferably provided with seal means to facilitate maintenance of the pressurised state. In one form the seal means are provided in the form of shaft seals. In a further form the seal means are provided in the form of housing seals.

In accordance with the present invention there is further provided a method for the pressurised recirculation of organic material, the method comprising the method steps of pressurising a reactor vessel in which a volume of organic material has been positioned and recirculating that volume of organic material to the reactor vessel whilst maintaining the pressurised state, wherein the organic material is largely solids.

Preferably, the recirculation of the organic material requires the passage of the organic material outside the confines of the reactor vessel and its reintroduction thereto.

Still preferably, the organic material is dewatered in the reactor vessel prior to recirculation and whilst under pressurised conditions.

Yet still preferably, the recirculation results in the organic material being conveyed in a substantially sealed manner from an outlet of the reactor vessel to an inlet thereof. Additional dewatering of the organic material preferably occurs as the organic material is recirculated.

Preferably, the moisture content of the conveyed organic material is reduced to about 40 to 60% during recirculation to the reactor vessel.

Arched or radial stress fields are preferably formed in the recirculated organic material as a result of decreased consolidation pressure in a base of the reactor vessel, whereby approximately uniform flow of the organic material from the reactor vessel is facilitated.

BRIEF DESCRIPTION OF THE DRAWINGS

The present invention will now be described, by way of example only, with reference to one embodiment thereof and the accompanying drawings, in which:—

FIG. 1 is a schematic representation of an apparatus for the pressurised recirculation of organic material in accordance with the present invention.

BEST MODE(S) FOR CARRYING OUT THE INVENTION

In FIG. 1 there is shown an apparatus 10 for the pressurised recirculation of organic material, for example the organic fraction of municipal solid waste ("OFMSW"). The apparatus 10 comprises a reactor vessel 12 having an organic material inlet 14 and an organic material outlet 16. Two arrays 18 of conveyors means, for example first outlet conveyors 20, are provided at the reactor vessel outlet 16. The first outlet conveyors 20 are arranged to convey material (not shown) from the reactor vessel 12 outwardly or laterally with respect to the outlet 16, and into second outlet conveyors 22 arranged to extend transversely with respect to the first outlet conveyors 20.

The arrays 18 back onto one another and convey material in substantially opposed directions to respective opposed sides of the outlet 16. A single central conveyor 24 is provided beneath the point at which the arrays 18 meet. The central conveyor collects material from a central column or screen (not shown) in the reactor vessel 12 which is used for liquid drainage when submerged. During solids recirculation this column in effect 'grates' the OFMSW as it travels downwardly. The solids that pass through the screen are collected by the central conveyor 24. The central conveyor 24 conveys material to an intermediate conveyor 26 that passes any material therein to the respective second outlet conveyor 22.

The second outlet conveyors 22 are arranged to direct material to respective third, or dewatering press conveyors 28, from which it may then be passed through an intermediate conveyor 29, a fourth conveyor 30, a fifth conveyor 32, a sixth conveyor 34 and a seventh conveyor 36.

The fifth conveyor 32 is fed by an eighth conveyor 38 with organic waste material from a materials recycling facility (not shown). A ninth conveyor 40 is provided, by which materials may be unloaded from the vessel 12 when the batch is complete.

Each of the conveyors 22 and 29 are provided with dewatering means, for example 180° screens (not shown), by which the material being conveyed therein may be gravity dewatered. The dewatering press conveyors 28 remove the majority of the liquid in the organic material by physically pressing the material against a 360° screen (not shown). A series of fluid lines 42 are provided from these conveyors 22, 24, 28 and 29 feeding to a fluid outlet 44. Each of the lines 42 have provided therein a valve means 46 for control of fluid flow therethrough.

A biogas outlet 58 is provided in the reactor vessel 12 and communicates with a biogas line 60. A series of fluid inlets 62 are provided in the reactor vessel 12 and are fed from a fluid inlet line 64 and a series of branches 66 therefrom. Each of the branches 66 have provided therein valve means 68 for control of fluid flow therethrough.

The reactor vessel 12 and each of the conveyor means, for example conveyors 18, 20, 22, 24, 26, 28, 29, 30, 32, 34 and 36, such as are required in the potential recirculation of material from the reactor vessel 12, are capable of being pressurised and maintain that pressure during the recirculation of material from the organic material outlet 16 to the organic material inlet 14. For this purpose each of the conveyors 18, 20, 22, 24, 26, 28, 29, 30, 32, 34 and 36 are equipped with seal means, for example shaft seals and housing or casing seals at the connection points between consecutive housings and inspections ports. Further, there are valves 70 provided on each of the conveyors 38 and 40 that communicate with a feed end 72 of the fifth conveyor 32.

In use, the organic fraction of municipal solid waste ("OFMSW") from a materials recycling facility ("MRF") are directed to a reactor vessel 12 in which a process such as that described in International Patent Application PCT/AU00/00865 (WO 01/05729) is to be conducted, where the OFMSW is to be exposed to sequential treatment through anaerobic digestion and aerobic composting stages.

The anaerobic digestion stage involves the introduction of liquid to the OFMSW to create conditions optimal for the production of biogas. Biogas production may be increased by ensuring maximum flow of the liquid through the OFMSW. This is achieved by way of recirculation of the OFMSW whilst maintaining substantially anaerobic conditions. This requires the draining of free liquid from the reactor vessel 12 through the conveyors 22 and 24, and the fluid outlet 44. Then the OFMSW from within the reactor vessel 12 is recirculated from the material outlet 16, through the action of conveyors 18, 20, 22, 24, 28, 29, 30, 34 and 36, to the material inlet 14.

This process results in the recirculation and rearrangement of the OFMSW and the improved penetration of liquid once that liquid is reintroduced to the reactor vessel. This in turn improves biogas production relative to an OFMSW that hasn't been recirculated in this manner. The ability to conduct this process under pressure, without having to vent the reactor vessel 12 (without opening the vessel to the atmosphere), allows the process to be conducted more quickly to achieve a given result when compared with the time taken to achieve that same result, in terms of biogas production, if using this process without recirculation or if using a static dry batch anaerobic digestion system of the prior art.

It is also known that it is necessary to dewater the OFMSW before the reactor vessel 12 can be transitioned to aerobic conditions. The arrangement of the present invention is such that it allows for the moisture content of the OFMSW to be reduced to optimum content of about 40 to 60% as it transitions to aerobic conditions. In part this is achieved by way of gravity draining that occurs within the reactor vessel 12 and in part by way of additional dewatering. The additional dewatering is achieved by passing the OFMSW through conveyors 18, 20, 22, 28, 29, 30, 32, 34 and 36 such that any free liquid is drained via the 180° screens and also through mechanical dewatering achieved by way of press via conveyors 28 which squeeze the liquid from the material under pressure.

It is envisaged that there may be provided more than a single inlet 14 and more than a single outlet 16 in the reactor vessel 12 without departing from the scope of the present invention.

The recirculation of the OFMSW is understood to favourably contribute to the establishing of arched or radial stress fields in the OFMSW above the base of the reactor vessel 12 whereby the flow of that OFMSW is enhanced through the arrays 20 of first conveyors 18 and 20. This is caused by the reduction in consolidation pressure at the base of reactor vessel 12 through the formation of the arched stress fields.

The ability to return recirculated, rearranged, and substantially dewatered OFMSW to the reactor vessel 12 under pressure is understood to be advantageous in that it allows the maintenance of a given moisture content during the aerobic composting stage. Further, as noted above, the reactor vessel 12 need not be opened to atmosphere and thereby continual processing is possible. Still further, the penetration of air into the OFMSW is improved, thereby improving aerobic activity and hence overall efficiency of the process.

The recirculation of the OFMSW within the reactor vessel 12, whether under pressure or not (during the aerobic phase) is understood to enable the moisture content to be maintained, the generation of an arched or radial stress field above the base of the reactor vessel 12, and improved air penetration and a reduction in consolidation of the OFMSW.

It can be seen from the above description that the apparatus and method of the present invention allow for improved results from processes for the treatment of organic wastes that utilise anaerobic digestion and/or aerobic composting in a vessel.

The benefits of solids recirculation apparent to the Applicants in light of the above description include:
(i) Improved biogas production through recirculation and rearrangement of the OFMSW and improved liquid penetration;
(ii) Improved transition from the anaerobic digestion stage to the aerobic composting stage through faster dewatering of the OFMSW over conventional gravity drainage;
(iii) The maintenance of moisture content at optimum levels during the aerobic composting stage; and
(iv) The creation of radial stress fields that act to reduce consolidation pressure of the OFMSW, improving flow of the material through outlet 16 and greater porosity to allow better air flow through the OFMSW thus improving aerobic composting efficiency.

Modifications and variations such as would be apparent to the skilled addressee are considered to fall within the scope of the present invention. For example, whilst the above example has been described in terms of the processing of OFMSW, the apparatus and method of the present invention are equally applicable to other sources of organic waste, including for example only, a combination of MSW, kitchen waste and green waste.

The invention claimed is:
1. A method for the pressurised recirculation of organic material, the method comprising the method steps of:
pressurising a reactor vessel in which a volume of organic material has been positioned;
treating the organic material sequentially through an anaerobic digestion stage and an aerobic composting stage, wherein the anaerobic digestion stage and the aerobic composting stage occur within the same reactor vessel; and recirculating the volume of organic material from an outlet of the reactor vessel to an inlet of the reactor vessel through at least one conveyor means comprising both a seal means and a valve means whilst maintaining the pressurised state, wherein the organic material is solids.

2. The method according to claim 1, wherein the organic material is rearranged.

3. The method according to claim 1, wherein the organic material is dewatered in the reactor vessel prior to recirculation and whilst under pressurised conditions.

4. The method according to claim 3, wherein additional dewatering of the organic material occurs as the organic material is recirculated.

5. The method according to claim 1, wherein the moisture content of the conveyed organic material is reduced to about 40 to 60% during recirculation to the reactor vessel.

6. The method according to claim 1, wherein arched or radial stress fields are formed in the recirculated organic material as a result of decreased consolidation pressure in a base of the reactor vessel, whereby approximately uniform flow of the organic material from the reactor vessel is facilitated.

7. The method according to claim 1, wherein the organic material is the organic fraction of municipal solid waste.

8. The method according to claim 1, wherein the anaerobic digestion stage includes introducing liquid to the organic material positioned within the reactor vessel to produce biogas.

\* \* \* \* \*